US00PP24607P3

(12) United States Plant Patent
Cunill et al.

(10) Patent No.: US PP24,607 P3
(45) Date of Patent: Jul. 8, 2014

(54) VARIETY OF OLIVE TREE NAMED 'BITSYOAC'

(50) Latin Name: ***Oleo europaea* L.**
Varietal Denomination: BITSYOAC

(75) Inventors: Marisa Cunill, Barcelona (ES); Salvador Duran, Barcelona (ES)

(73) Assignee: Agromillora Iberia, S.L., Barcelona (ES)

( * ) Notice: Subject to any disclaimer, the term of this patent is extended or adjusted under 35 U.S.C. 154(b) by 51 days.

(21) Appl. No.: 13/507,201

(22) Filed: Jun. 12, 2012

(65) Prior Publication Data
US 2013/0333078 P1 Dec. 12, 2013

(51) Int. Cl.
*A01H 5/00* (2006.01)

(52) U.S. Cl.
USPC ..... Plt./158

(58) Field of Classification Search
USPC ..... Plt./158
See application file for complete search history.

*Primary Examiner* — Annette Para
(74) *Attorney, Agent, or Firm* — The Webb Law Firm

(57) ABSTRACT

A new and distinct olive tree used primarily for oil production that exhibits a compact growth habit, uniform and continuous production level, and high amounts of oleic acid content.

8 Drawing Sheets

Botanical classification: *Oleo europaea* L.
Varietal denomination: 'BITSYOAC'.

BACKGROUND OF THE INVENTION

The present invention comprises a new and distinct cultivar of olive tree known by the varietal name 'BITSYOAC'. The new variety was discovered in Barcelona, Spain in 1988 as a result of a planned breeding program. The new variety is the result of a cross between *Oleo europaea* L. 'Arbequina OLINT' (female parent, protected by U.S. Plant Pat. No. 18,600) and *Oleo europaea* L. 'Arbosana OLINT' (male parent, protected by U.S. Plant Pat. No. 18,598). The purpose of the breeding program was to develop a low vigor variety with a suitable tree structure, adapted to a high density production system, with a medium tolerance to *Spilocaea oleagina* (peacock leaf spot). The new variety exhibits a high productivity and precocity. Among other important traits, olive fruits are retained after reaching maturity allowing optimum mechanical harvesting with minimum loss.

The new variety exhibits similar small fruits and short and narrow leaves to both parents, but differs from both parents in its vigor and date of maturity. Further, the new variety is similar to 'Arbequina' in its semi-erect habit, fruit shape and small leaves. However, the new variety has a later date of maturity than 'Arbequina', exhibits a different leaf shape, has lower vigor, and a higher percentage of oleic acid than its female parent. The new variety has been trial and field tested and has been found to retain its distinctive characteristics and remain true to type through successive propagations. The following characteristics distinguish 'BITSYOAC' from other varieties known to the breeder:

1. Low vigor with a small trunk cross-section area;
2. High productivity;
3. Better cold tolerance than 'Arbosana';
4. Moderate resistance to *Spilocaea oleagina;*
5. Requires less pruning than most olive varieties;

6. Compact growth habit; and
7. Higher content of oleic fatty acid than most olive varieties

DESCRIPTION OF THE DRAWINGS

The accompanying photographic drawings illustrate the new variety with the color being as nearly true as is possible with color illustrations of this type.

DESCRIPTION OF THE PLANT

Figure 1:
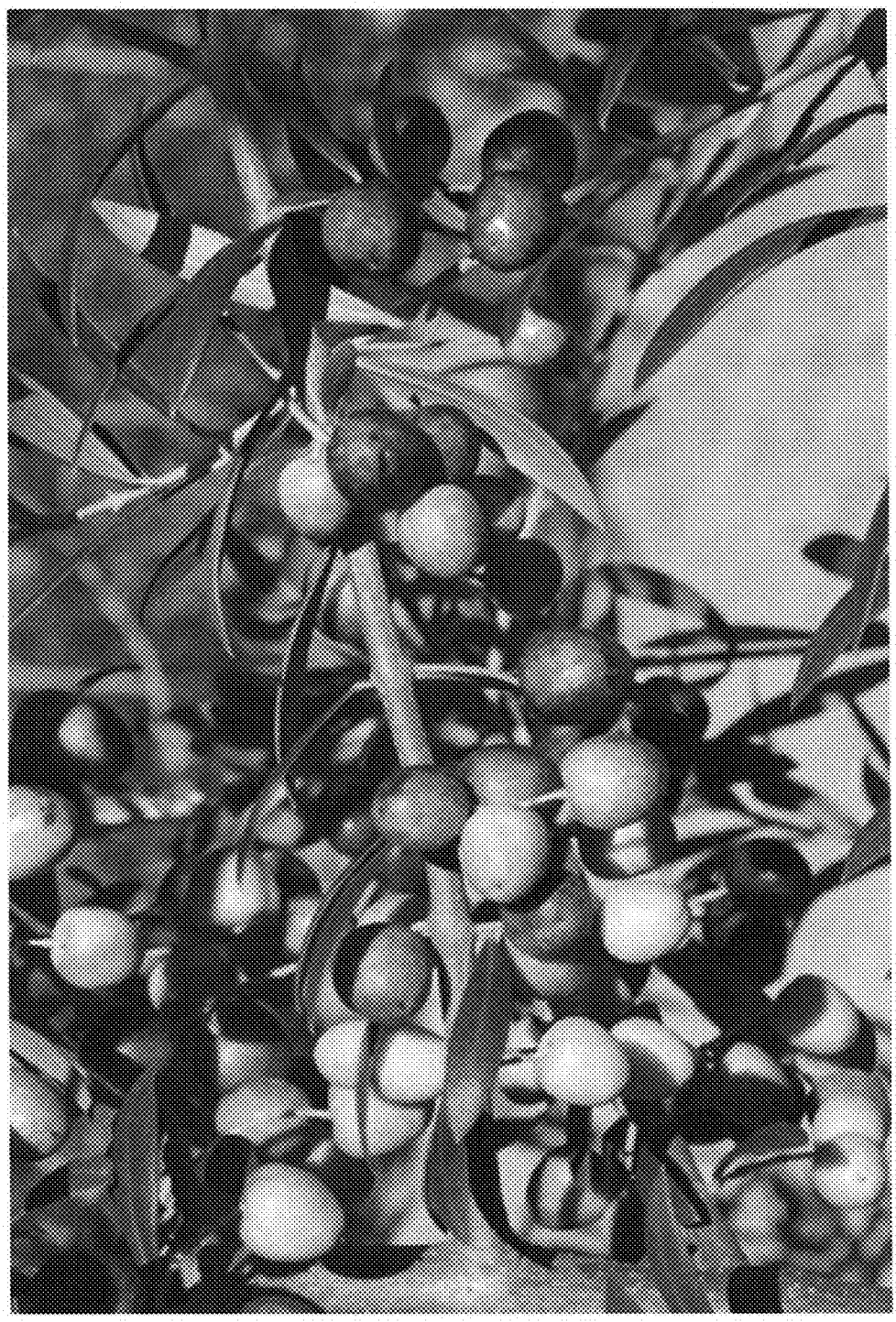
FIG. 1 shows the fruits of the new variety.
Figure 2:
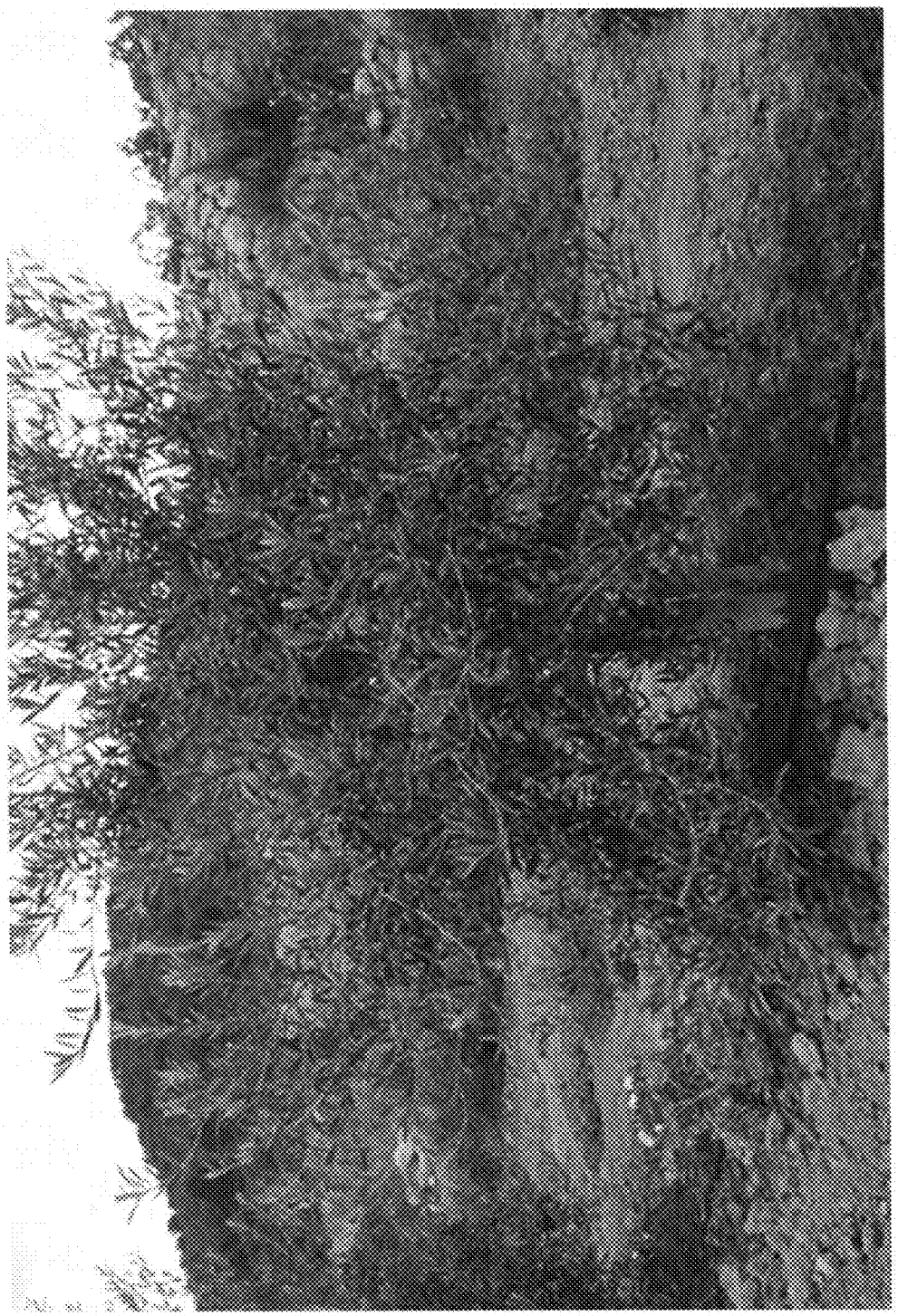
FIG. 2 shows an entire tree of the new variety.
Figure 3:
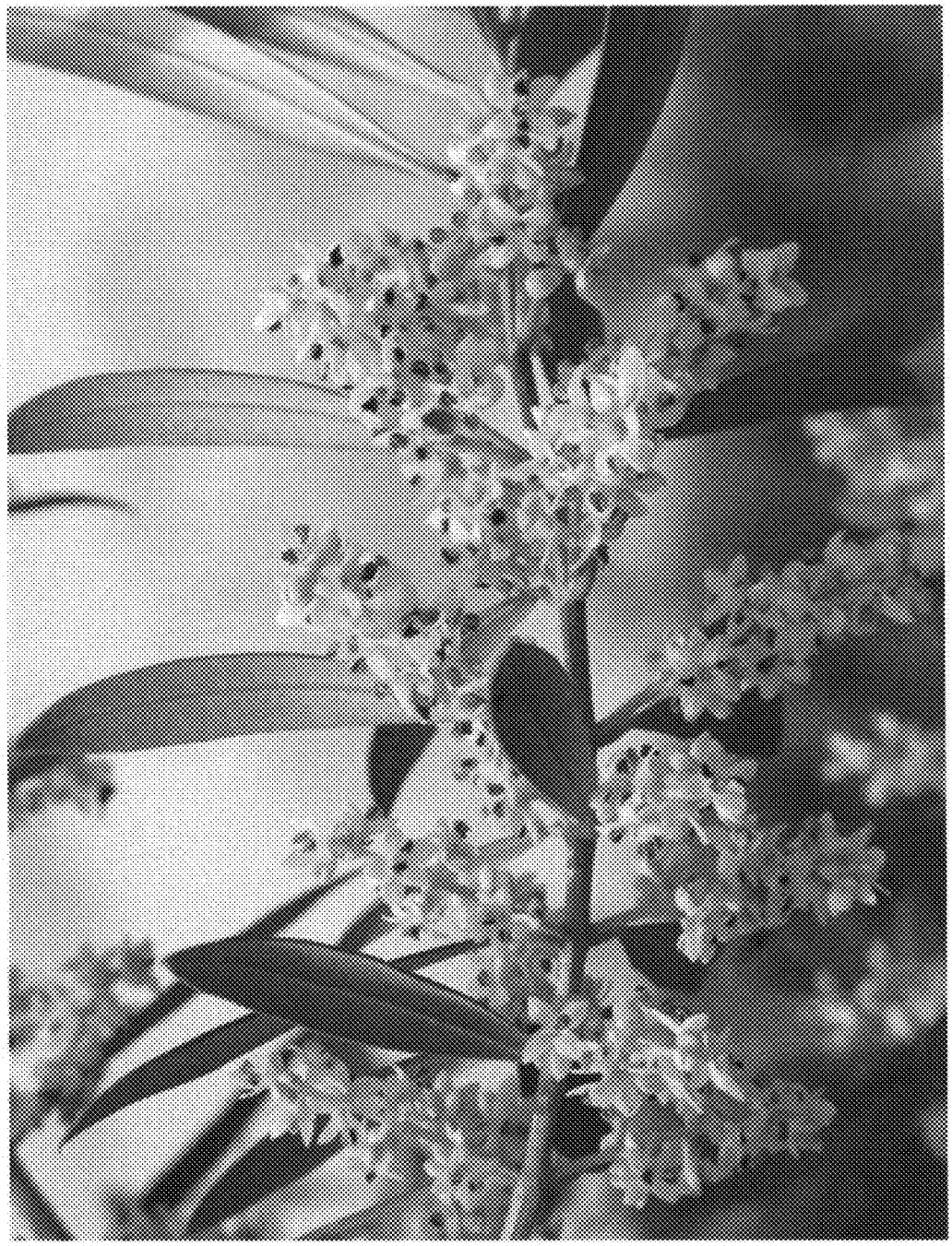
FIG. 3 shows the flowers of the new variety.
Figure 4:
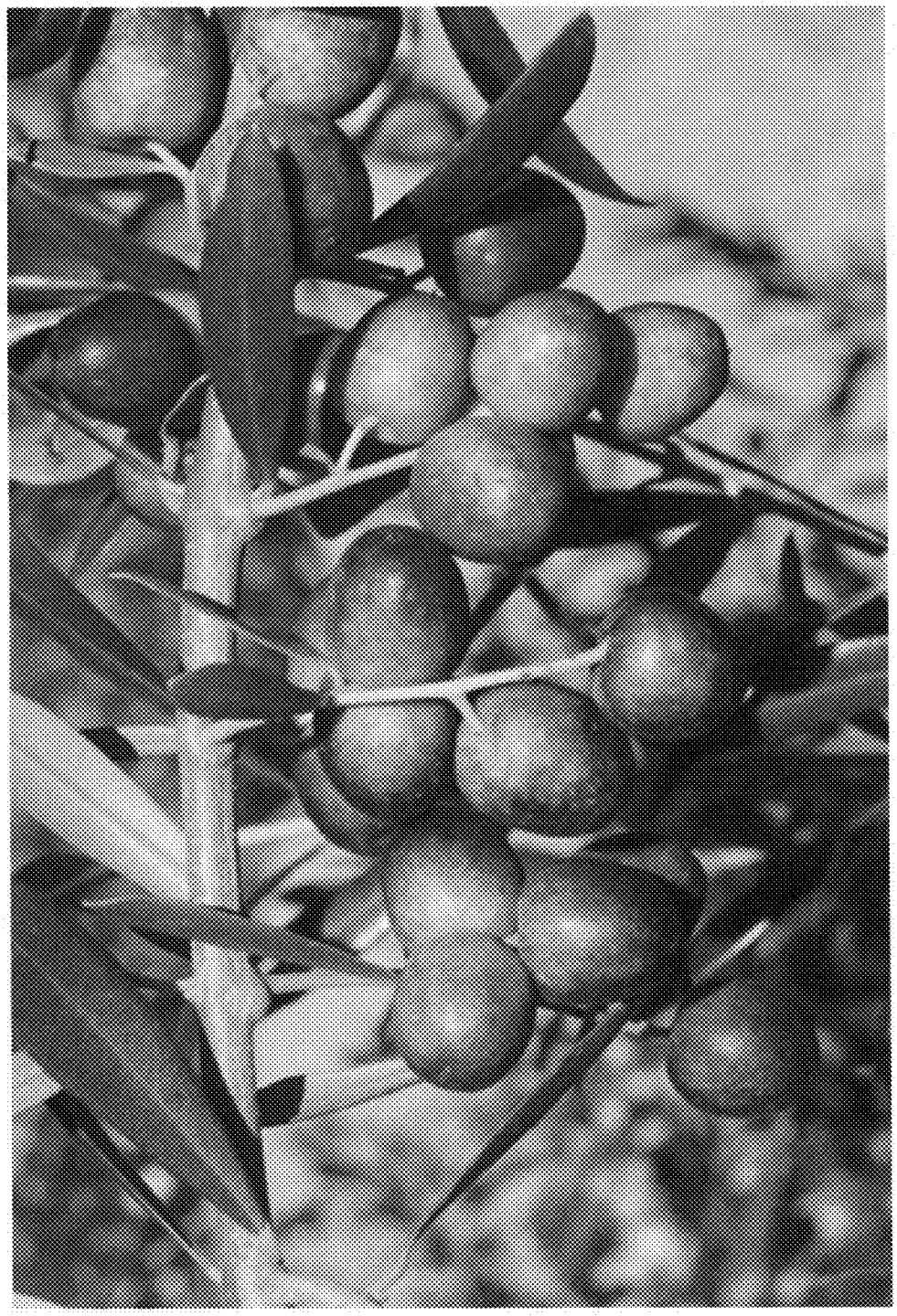
FIG. 4 is a close-up photograph of the fruits and leaves of the new variety.
Figure 5:
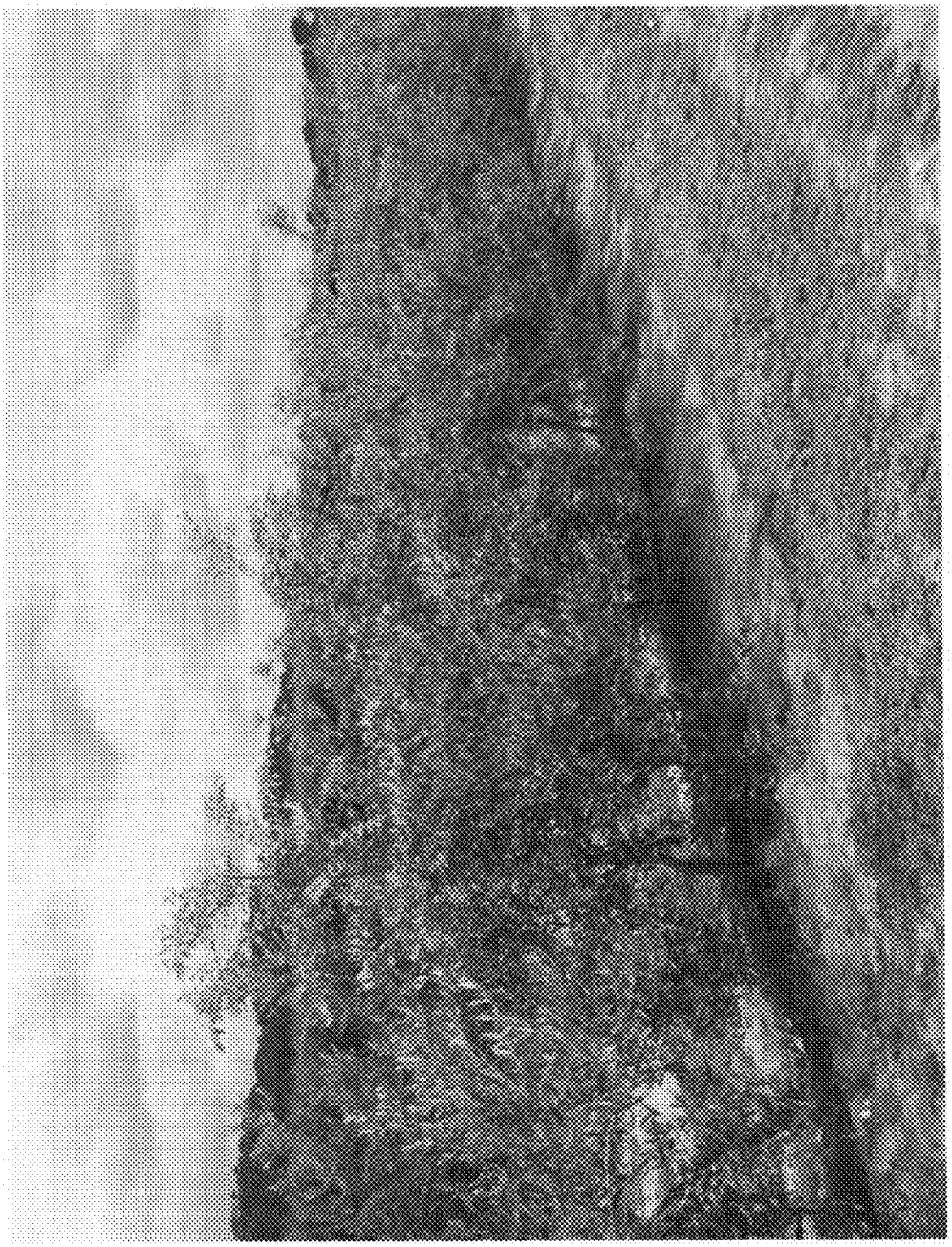
FIG. 5 shows a field of the new variety.
Figure 6:
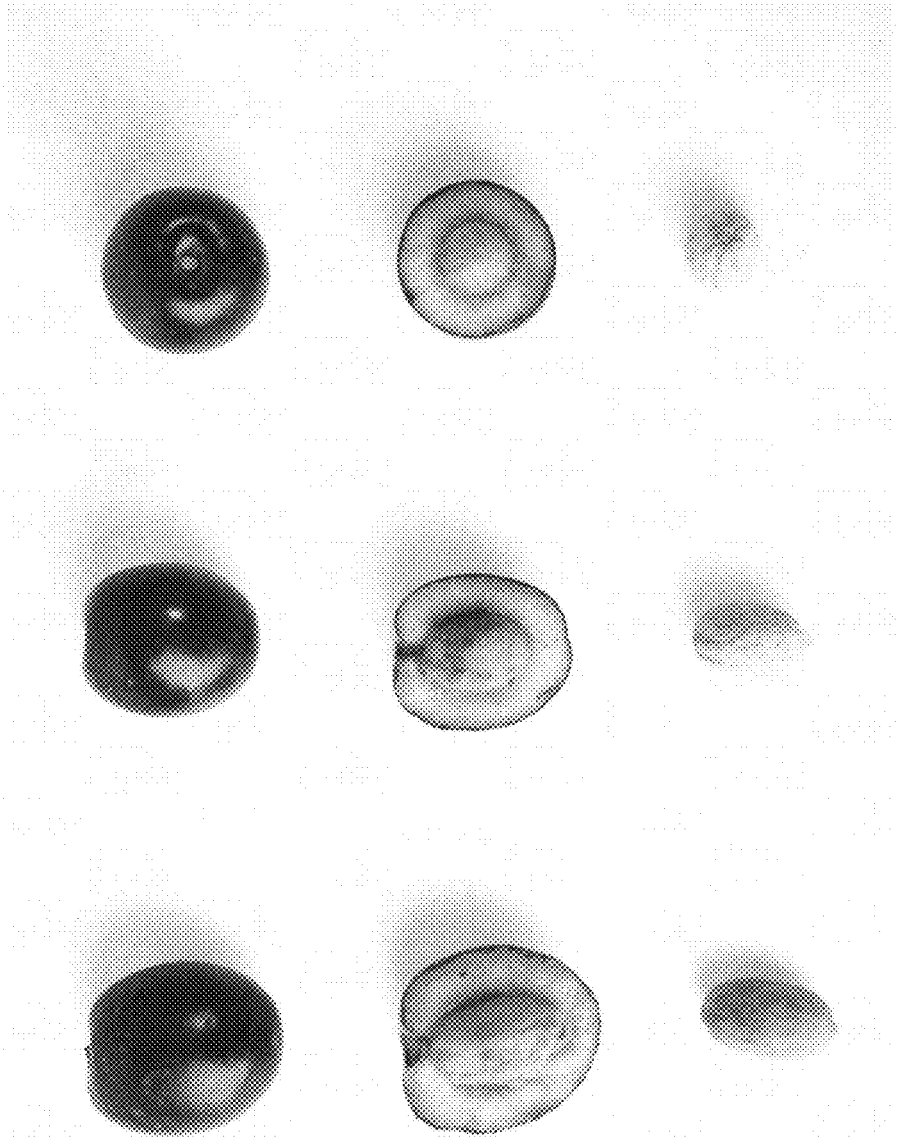
FIG. 6 shows whole and cut fruits of the new variety, as well as stones.
Figure 7:
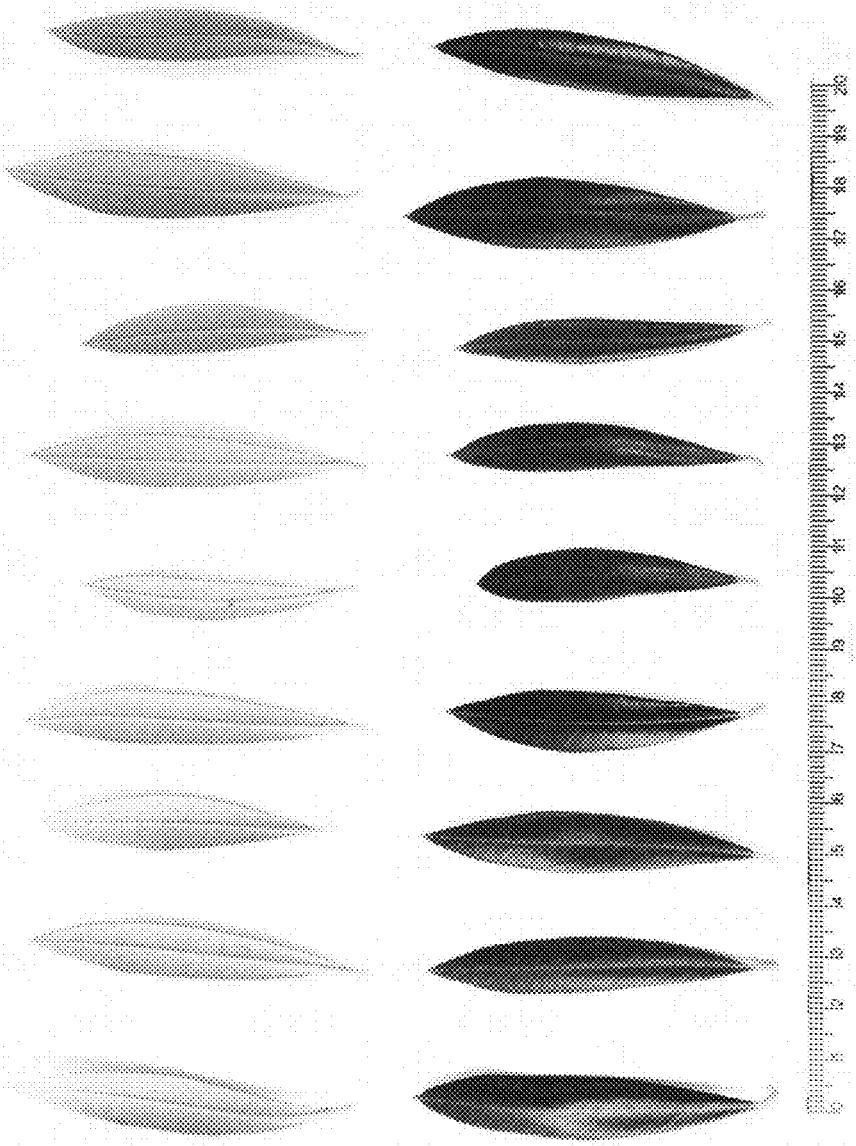
FIG. 7 shows the upper and lower leaf surfaces of the new variety.
Figure 8:
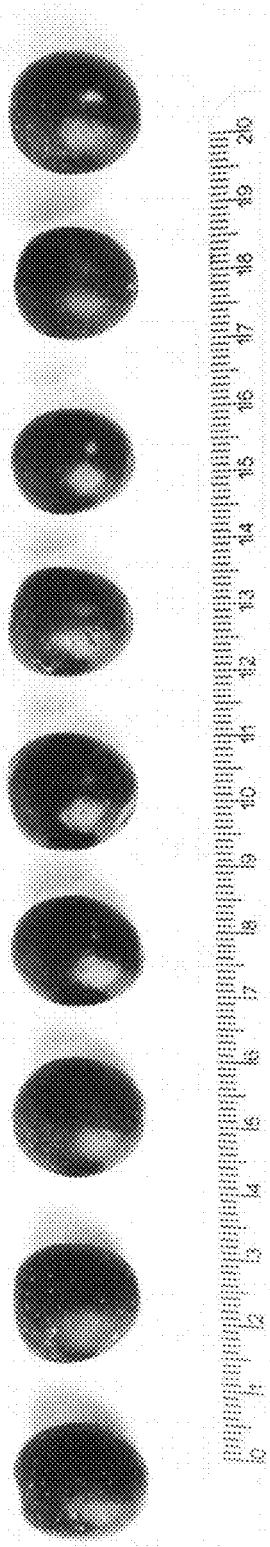
FIG. 8 shows detached fruits of the new variety.

The following detailed description sets forth the characteristics of the new cultivar. The data which defines these characteristics was collected under natural daylight on plants produced by semi-ligneous cuttings carried out in Barcelona, Spain. The plants were grown under normal field conditions with drip irrigation 40 liter containers. Color designations are presented with reference to the "Dictionary of Color" by A. Maerz and M. Rea Paul, Second Edition (1950).

TREE

Age: 10 years.
Size:
*Height.*—5.56-7.22 feet (200-220 cm.).
*Width.*—5.08-5.41 feet (155-165 cm.).
Vigor: Low.
Density: Sparce.

Form: Semi-erect.
Production: Production level is uniform and continuous with good oil production.
Growth: Reaches definite size in about 10 years.
Bearing: Regular.
Trunk:
*Length.*—34.3-44.9 inches (87-114 cm.).
*Diameter.*—3.0-3.1 inches (7.5-8.0 cm.).
*Surface texture.*—Smooth.
*Bark color.*—Plate 22 C-1 (dusty green).
*Lenticels.*—Length: Small; 1.5-2.0 mm. (0.06-0.08 inches). Width: 0.5-1.0 mm. (0.02-0.04 inches). Density: Few.
Main branches:
*Length.*—37.8-39.0 inches (96-99 cm.)/35.8-42.5 inches (91-108 cm.).
*Diameter.*—1.3-2.2 inches (3.2-5.5 cm.)/1.3-1.7 inches (3.4-4.2 cm.).
*Surface texture.*—Smooth.
*Color.*—Plate 22 C-1 (dusty green).
*Form.*—Semi-erect.
*Average angle.*—35°-45°.
*Bud arrangement.*—Opposite.
*Lenticels.*—Length: Small; 2-3 mm. (0.08-0.12 inches). Width: 1-2 mm. (0.04-0.08 inches). Shape: Rounded. Density: Scarce, less than on the trunk.
Leaves:
*Length.*—44-66 mm. (1.73-2.6 inches).
*Width.*—10-12 mm. (0.39-0.47 inches).
*Form.*—Elliptic-lanceolate.
*Texture.*—Grainy.
*Thickness.*—Medium.
*Base.*—Cuneate.
*Apex.*—Acute-rounded.
*Margin.*—Entire.
*Pubescence.*—Upper surface: Smooth, slightly grainy. Lower surface: Smooth, slightly pubescent.
*Color.*—Young leaves: Upper surface: Plate 24 L-4. Lower surface: Plate 20 F-3. Mature leaves: Upper surface: Plate 24 L-3. Lower surface: Plate 20 F-5.
*Petiole.*—Shape: Rounded with an incipient central groove. Length: 2-3 mm (0.08-0.12 inches). Diameter: 1-1.5 mm (0.04-0.06 inches). Color: Plate 21 J-1 (grape green).
*Veins.*—Presence: Only one central vein. Color: Upper surface: Plate 21 L-6 (parrot green). Lower surface: Plate 21 L-2 (moss green).
Inflorescence:
*Bloom timing.*—End of May.
*Blooming period.*—From the middle of May to the end of May.
*Number of flowers per inflorescence.*—9-16.
Flower:
*Color.*—Plate 1 A-1 (white).
*Pollen color.*—Plate 9 K-3 (yellow, empire Y).
*Fragrance.*—Very mild.
*Pistil number.*—1.
*Stamen number.*—15-25.
Sepal:
*Length.*—1 mm.
*Width.*—Less than 1 mm.
*Apex.*—Acute.
*Margin.*—Entire.
*Upper and lower surface color.*—Plate 17 E-5.
Pedicel:
*Diameter.*—Less than 1 mm.
*Texture.*—Smooth.
*Color.*—Plate 17 E-3 (butter yellow).
Corolla segment:
*Number per flower.*—4.
*Length/width.*—Small; about 4 mm. (0.16 inches)
*Color.*—Plate 1 A-1 (white).
Calyx lobe:
*Number per flower.*—4.
*Color.*—Plate 17 E-5.
Fruit (drupe):
*Maturity when described.*—The middle of December (Barcelona, Spain).
*Date of picking at designated location.*—The first week of November.
*Average fruit production per tree.*—9 kg on 4-year-old plants in axe formation with an extremely high density system.
*Stem.*—Length: 2-10 mm. (0.08-0.39 inches). Width: 1-1.5 mm. (0.04-0.06 inches).
*Size.*—Axial diameter: Average 16.1 mm. (0.63 inches); 14.8-18.1 mm. (0.58-0.71 inches). Transverse diameter: Average 13.6 mm. (0.54 inches); 12.6-14.6 mm. (0.5-0.57 inches).
*Form.*—Globose.
*Cavity.*—Shape: Circular. Depth: Medium. Breadth: 2-3 mm. (0.08-0.12 inches).
Skin:
*Thickness.*—Thin.
*Texture.*—Smooth.
*Tendency to crack.*—None.
*Color.*—Plate 48 L-12.
Flesh:
*Aroma.*—None.
*Color.*—Plate 20 C-1 (eucalyptus green).
*Eating quality.*—Mainly used for oil production.
Stone:
*Length.*—Average 10.6 mm. (0.42 inches); 8.8-11.2 mm. (0.35-0.44 inches).
*Width.*—Average 6.8 mm. (0.27 inches); 6.3-7.5 mm. (2.5-3.0 inches).
*Thickness.*—1.6-2.1 mm. (0.06-0.08 inches).
*Form.*—Obovate; shape of cross-section is elliptical.
*Apex.*—Rounded.
*Base.*—Truncate.
*Color.*—Plate 12 C-3 (old ivory).
*Mucron.*—Absent.
*Ridges.*—Distribution excluding apex, regular.

GENERAL

Use: For oil production.
Virgin oil fatty acid percentages (oleic acid, linoleic acid, palmitic acid, etc.):

Chemical Analysis

| | Percent of Total Oil Content |
|---|---|
| C18:1 Oleic acid | 75.0 |
| C18:2 Linoleic acid | 7.1 |
| C16:0 Palmitic acid | 13.2 |

-continued

| Chemical Analysis | |
|---|---|
| | Percent of Total Oil Content |
| C16:1 Palmitoleic acid | 1.5 |
| C18:0 Estearic acid | 1.5 |
| C18:3 Linolenic acid | 0.7 |

M/P ratio (monosaturated fats/polysaturated fats): 9:9.
K225 (bitterness): 0.42.
Polyphenols (ppm caffeic acid): 209.
Shipping quality: Good.
Keeping quality: Good.

Tree winter hardiness: Low.
Bud winter hardiness: Low.
Drought tolerance: Good.
Disease resistance: Moderate resistance to *Spilocaea oleagina*.
Observed plant/fruit resistance: Tolerant to *Spilocaea oleagina*.
Observed plant/fruit susceptibility: None observed.
Observed plant cold resistance/susceptibility: Moderately resistant to cold.

I claim:

1. A new and distinct variety of olive tree, as illustrated and described herein.

* * * * *